United States Patent
Mueller

(10) Patent No.: US 7,437,905 B1
(45) Date of Patent: Oct. 21, 2008

(54) GAS SENSOR WITH ONE POINT CALIBRATION

(75) Inventor: Michael M. Mueller, Portland, OR (US)

(73) Assignee: Digital Control Systems, Inc., Portland, OR (US)

( * ) Notice: Subject to any disclaimer, the term of this patent is extended or adjusted under 35 U.S.C. 154(b) by 0 days.

(21) Appl. No.: 11/931,259

(22) Filed: Oct. 31, 2007

Related U.S. Application Data

(60) Division of application No. 11/108,947, filed on Apr. 18, 2005, now Pat. No. 7,326,922, which is a continuation-in-part of application No. 10/183,921, filed on Jun. 26, 2002, now Pat. No. 6,882,426.

(51) Int. Cl.
*G01N 21/84* (2006.01)
*G01N 21/61* (2006.01)

(52) U.S. Cl. .............. 73/1.06; 250/252.1; 702/100

(58) Field of Classification Search ......... 73/1.06–1.07; 250/252.1; 702/100
See application file for complete search history.

(56) References Cited

U.S. PATENT DOCUMENTS

| | | | |
|---|---|---|---|
| 3,428,401 A | 2/1969 | Buzza | |
| 3,702,397 A | 11/1972 | Firth et al. | |
| 4,323,777 A | 4/1982 | Baskins et al. | |
| 4,464,653 A | 8/1984 | Winner | |
| 4,662,755 A | 5/1987 | Aoki et al. | |
| 5,125,742 A | 6/1992 | Wilks, Jr. | |
| 5,163,332 A | 11/1992 | Wong | |
| 5,239,492 A * | 8/1993 | Hartwig et al. | 73/1.07 X |
| 5,272,090 A | 12/1993 | Gavish et al. | |
| 5,550,053 A | 8/1996 | Salpeter | |
| 5,874,737 A | 2/1999 | Bytyn et al. | |
| RE36,277 E | 8/1999 | Black et al. | |
| 6,033,459 A | 3/2000 | Hase | |
| 2004/0191120 A1 | 9/2004 | Yanagawa | |
| 2007/0034792 A1 | 2/2007 | Zhang | |

* cited by examiner

*Primary Examiner*—Thomas P Noland
(74) *Attorney, Agent, or Firm*—Marger Johnson & McCollom, P.C.

(57) ABSTRACT

System and method for calibrating a sensor comprises a detector capable of detecting electromagnetic radiation at least at a radiation wavelength of interest, an analyzer capable of determining concentration values in response to the detected radiation, and a calibrator capable of automatically calibrating the analyzer in response to at least one concentration value. A method for operating a calibrator comprises receiving an initiation signal capable of initiating the calibrator, automatically obtaining concentration values in response to the initiation signal, and automatically determining a calibration value from the obtained concentration values. In an embodiment, the calibrator automatically determines when a calibration gas equilibrates within a sample chamber.

9 Claims, 6 Drawing Sheets

GAS SENSOR WITH ONE POINT CALIBRATION

RELATED APPLICATION DATA

This application is a division of copending, commonly-assigned U.S. Ser. No. 11/108,947, filed Apr. 18, 2005, which is a continuation-in-part of U.S. Ser. No. 10/183,921, filed Jun. 26, 2002, now U.S. Pat. No. 6,882,426, issued Apr. 19, 2005, the entire contents of which are incorporated herein by reference.

FIELD OF THE INVENTION

This invention relates generally to gas sensors, and more specifically to calibration of sensors having sample chambers for non-dispersive infrared measurement of gas concentration.

BACKGROUND OF THE INVENTION

Many techniques exist for sensing a constituent gas concentration within a gas sample. Non-dispersive infrared (NDIR) techniques infer the concentration of a constituent gas by measuring the gas sample's ability to absorb electromagnetic radiation. By examining absorption in a wavelength band where absorption is dominated by one constituent gas, relatively simple NDIR sensors can accurately measure concentration of that gas as a function of radiation absorption. For instance, carbon dioxide ($CO_2$) detectors often measure absorption at a 4.2-micron wavelength, where $CO_2$ strongly absorbs. For other gases, other visible or infrared bands can be selected.

To ensure accurate determination of the gas concentrations, a sensor may require periodic calibration. The typical calibration process includes providing a calibration gas with a known concentration to sample chamber via gas port, manually accessing electronics to obtain gas concentration data as each is determined, waiting for the calibration gas to equilibrate within sensor, and manually adjusting one or more controls within sensor electronics to set the measured equilibrium gas concentration equal to the known concentration value of the calibration gas. This process, however, is highly dependent upon the skill of the human technician. For instance, the technician is required to manually access sensor electronics to retrieve the reported gas concentrations in real-time and to manually adjust sensor electronics based on the reported concentration values. The technician typically must perform a real-time mathematical conversion on each reported concentration value, e.g., a conversion from volts [V] or millivolts [mV] to parts per million [ppm]. In some instances, the manual adjustment of sensor can be sensitive and time-consuming, especially if there is a lag time between the adjustment and the corresponding reported gas concentration. The technician must also exercise some judgment as to when the calibration gas has reached equilibrium within sample chamber. Sensor, further, may be inconveniently located such that the technician cannot gain the physical access required to perform the manual calibration.

The invention is an improved calibration system and method of calibrating a gas sensor that automatically calibrates the sensor.

DESCRIPTION OF THE DRAWINGS

The invention may be better understood by reading the following detailed description, which proceeds with reference to the accompanying drawings, wherein.

DETAILED DESCRIPTION

Reference will now be made in detail to embodiments of the present invention, examples of which are illustrated in the accompanying drawings. However, the present invention is not limited to the illustrated embodiments, and the illustrated embodiments are introduced to provide easy and complete understanding of the spirit and scope of the present invention.

Figure 1:
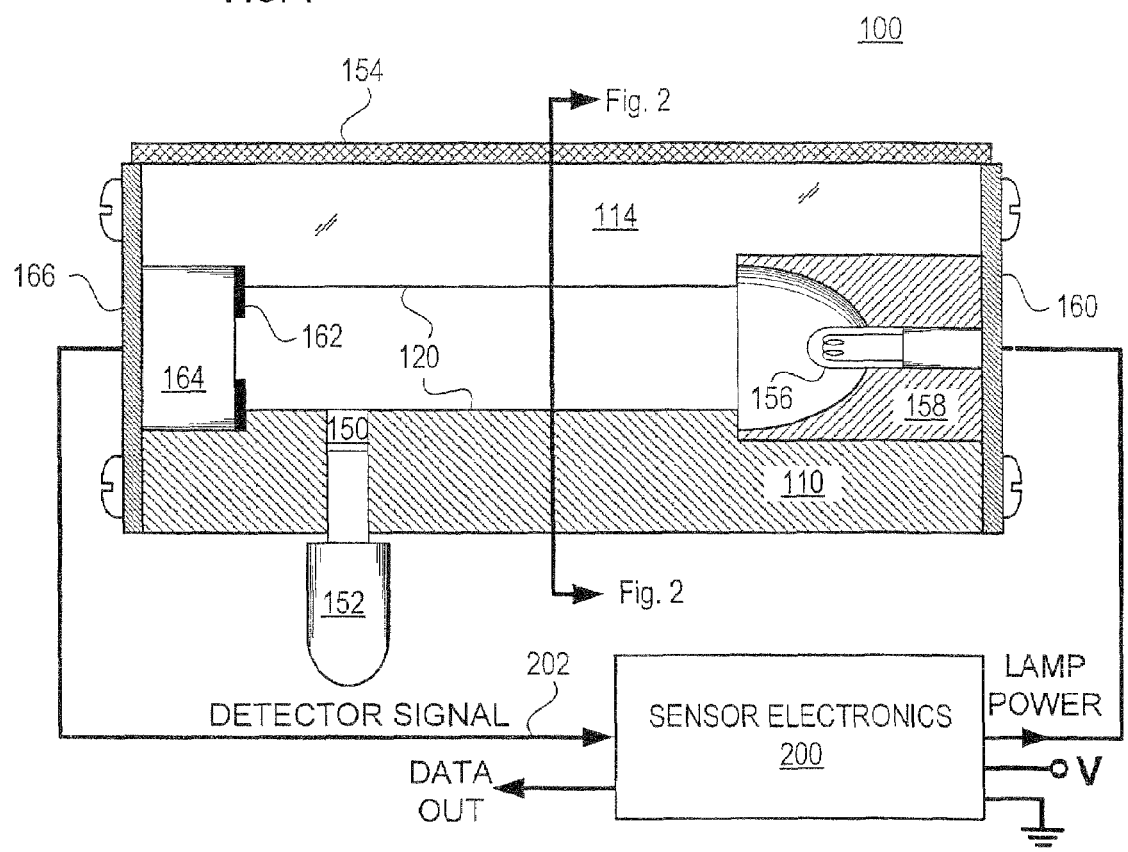
FIGS. 1 and 2 show two cross-sectional views of a gas sensor according to one embodiment of the present invention employing a diffusion chamber.
Figure 2:
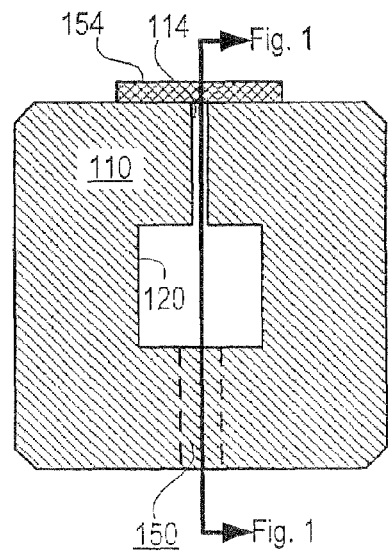

A typical sensing system includes a chamber capable of receiving a gas sample through a gas port, a source capable of generating electromagnetic radiation, and a detector capable of detecting the generated electromagnetic radiation after its propagation through the chamber. A sensor 100 designed by the inventor of the present invention, is shown in FIGS. 1 and 2. Sensor 100 comprises a diffusion-type sample chamber 110, a source assembly 156, 158, and 160, detection assembly 162, 164, and 166, and one or more gas ports. Sample chamber 110 is shown in cross-section along the direction of electromagnetic radiation propagation in FIG. 1, and in cross-section perpendicular to the direction of electromagnetic radiation propagation in FIG. 2 (the source and detection assembly are not cross-sectioned, and are omitted from FIG. 2 for clarity). Chamber 110 is preferably formed of extruded aluminum with die marks scoring the inner surface along the direction of light propagation, followed by etching and chromating as described in incorporated U.S. Pat. No. 6,882,426, to produce a semidiffusive inner surface.

Slot 114 serves sensor 100 as a gas diffusion port to allow gas to diffuse into a rectangular passageway 120 disposed lengthwise in chamber 110. Slot 114 can be covered with some sort of porous medium 154, such as Vent Tape 394 (a trademark of 3M), to prevent insects, spiders, gross dust, and large solid objects from entering chamber 100. Gas port 150 is used for injection of calibration gas, and is normally blocked by cap 152. Sensor 100 accepts the source assembly, comprising incandescent bulb 156, elliptical reflector 158, and mounting plate 160, into a machined hole in one end of chamber 110. Sensor 100 accepts the detector assembly, comprising an aperture stop and filter 162, a detector 164, and a mounting plate 166, in a second machined hole in its opposite end of chamber 110. Electronics 200 is capable of driving the source, receiving measurements 202 from detector 164, determining a gas concentration from each measurement, and reporting each gas concentration datum to a display network, controller, or other utilization device (not shown) as each datum is determined.

Figure 3A:
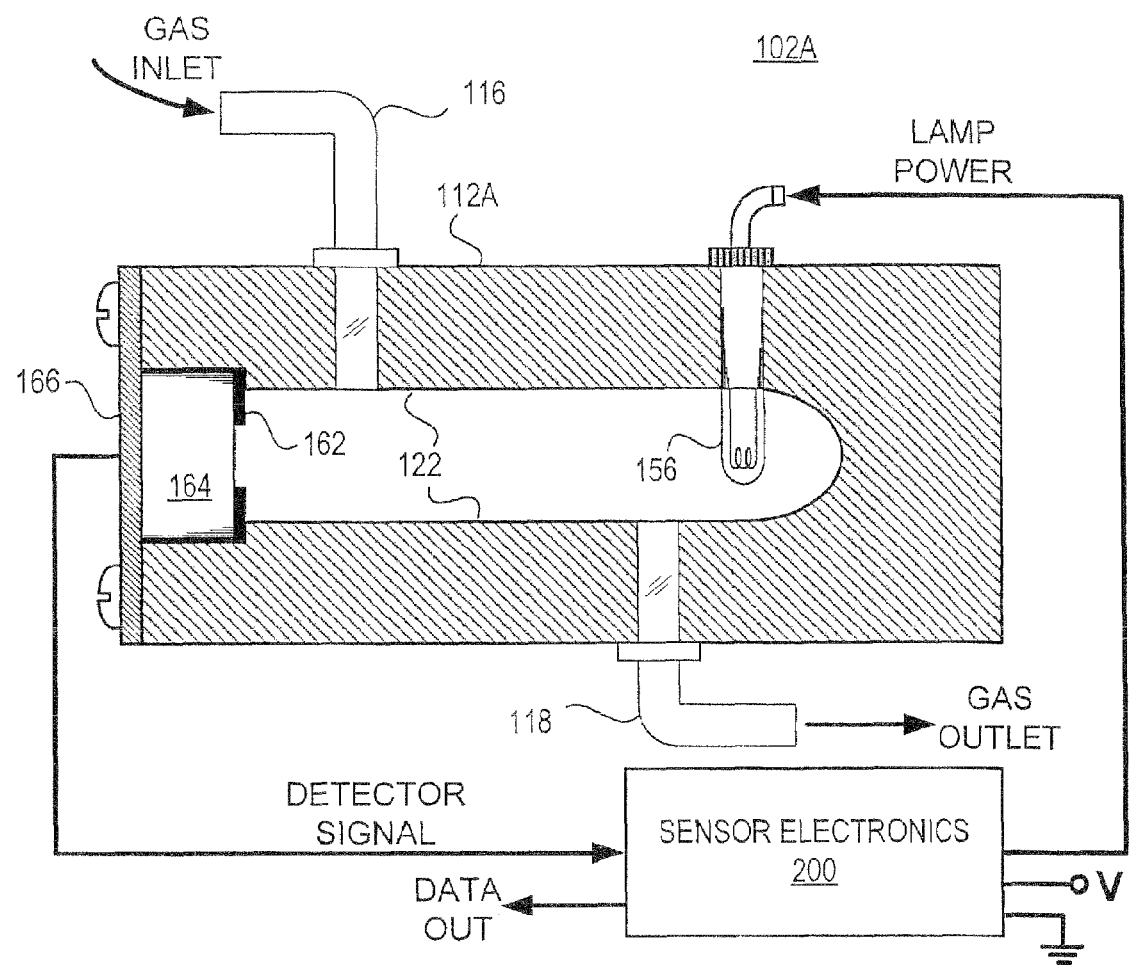
FIG. 3A shows an alternative embodiment of the invention employing a sample-draw chamber and FIG. 3B shows a similar embodiment employing a diffusion chamber.

FIG. 3A is a cross-sectional view of an alternative embodiment of a sensor 102A, which employs a sample-draw chamber 112A. The general arrangement is similar to sensor 100 and so only a few differences merit mention. The chamber 112A has a cylindrical blind bore forming gas passageway 122 in chamber 112. Gas inlet and outlet tubes 116, 118 are ported into sides of the chamber 112 and lamp 156 is ported into a side of chamber 112 near its blind end.

Figure 3B:
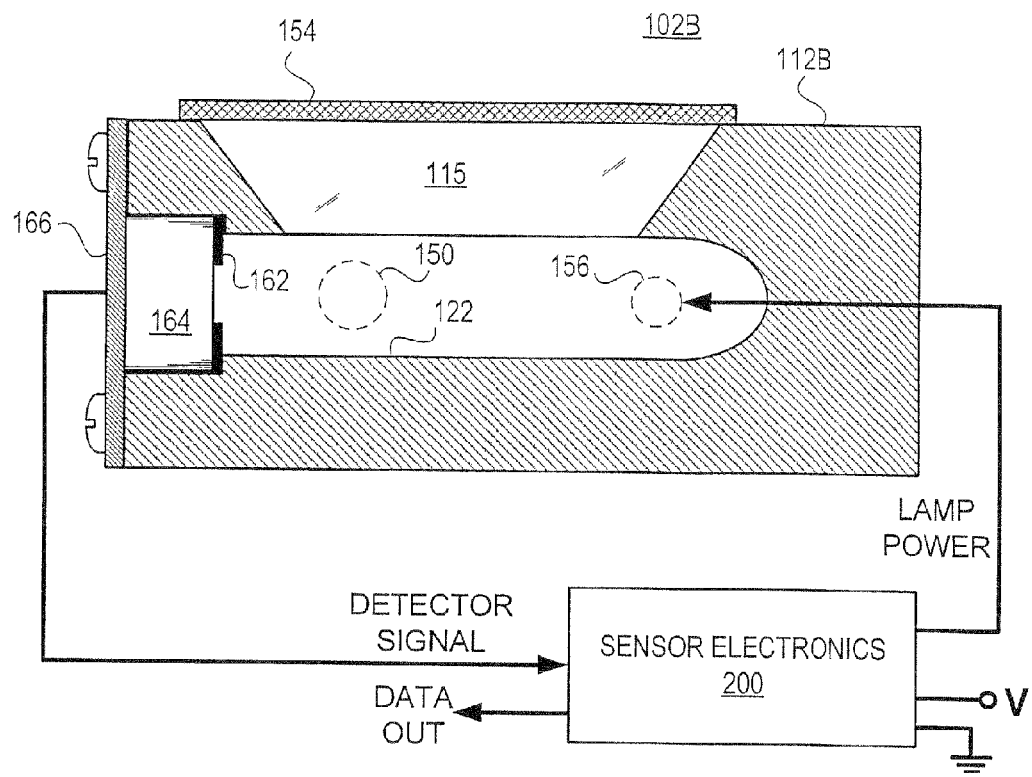

The embodiment of FIG. 3B is similar to that of FIG. 3A but the chamber 112B is configured as a diffusion-type chamber with a slot 115 along one side, instead of gas inlet and outlet ports 116, 118, to permit ambient gases to diffuse into and out of the chamber through porous medium 154. The blind bores of both chambers 112A and 112B are formed by drilling or machining a cylindrical bore into a chamber blank or billet of metal, preferably rectilinear in shape and preferably formed of aluminum. The drilling or machining operation is performed so as to leave circumferential grooves or roughness around the cylindrical bore, following which the chamber is etched and chromated as described in incorporated U.S. Pat. No. 6,882,426. The amount of roughness can be varied but together with the etching and chromating should produce a semidiffusive surface to spread light or IR radiation traversing the bore lengthwise. In this case, however, the machining produces an inner surface that is preferentially roughened along the length of the bore, perpendicularly to the direction of light propagation, rather than across the bore and along the direction of light propagation as in the embodiment of FIGS. 1 and 2 and as further described in incorporated U.S. Pat. No. 6,882,426.

Figure 3C:
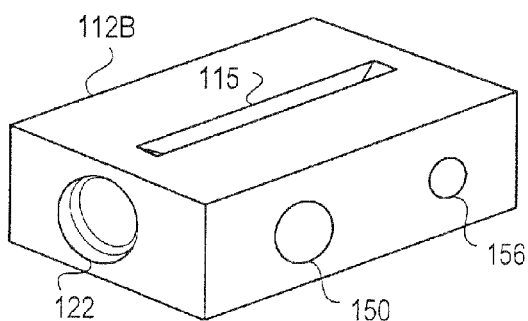
FIGS. 3C and 3D show embodiments of the diffusion chamber of FIG. 3B.
Figure 3D:
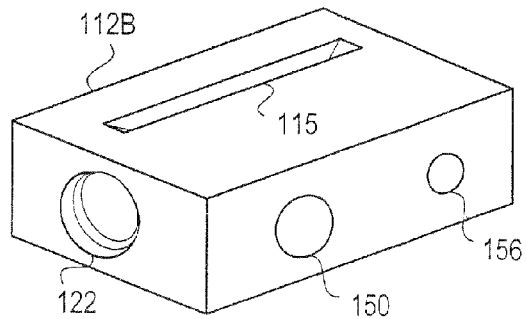

As shown in FIGS. 3C and 3D, the lengthwise diffusion slot 115 in the embodiment of FIG. 3B may be positioned either centrally in the chamber, along its long axis, so that it intersects the inner surface approximately radially relative to the axis of the bore, or may be offset to one side so that it intersects the inner surface approximately tangentially relative to the inner surface. In the latter position, the tangential side of the slot serves to reflect radiation back into the chamber.

The present invention is directed to automated sensor calibration. Typically, sensor calibration is heavily reliant upon the skill and judgment of a human technician, and thus the calibration may be time-consuming or inaccurate. The addition of a calibrator to sensor electronics 200 enables automated calibration of sensor 100, thus overcoming the above-recited deficiencies of manual calibration.

Figure 4:
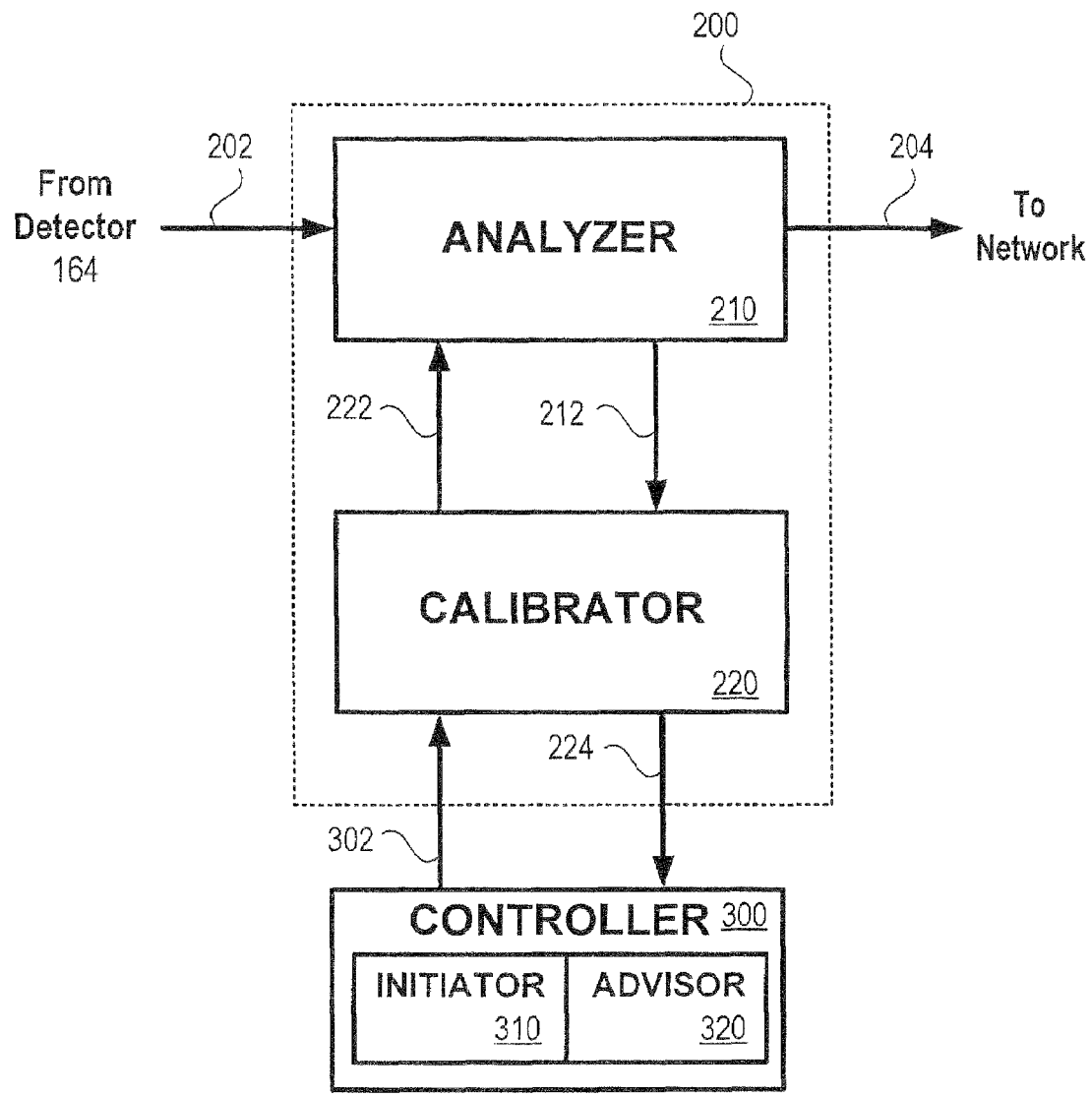
FIG. 4 illustrates, in block form, an implementation of sensor electronics with a controller useful with embodiments of the present invention.

FIG. 4 shows an implementation of sensor electronics 200 and controller 300 useful with various embodiments of the present invention. Sensor electronics 200 comprises analyzer 210 and calibrator 220, which may be integrated into a monolithic integrated circuit, hardwired in a hybrid module using any number of discrete logic and/or other components, implemented in a dedicated processor system that includes a microcontroller, a microprocessor, or multiple communicating processors capable of implementing software programs or algorithms comprised in a computer-readable medium, or any combination thereof.

Analyzer 210 receives electrical signals 202 from detector 164 and determines concentration values 204 from these electromagnetic radiation measurements 202 and a control value. The analyzer produces a concentration value 204 that corresponds to the concentration of a constituent gas within a sample chamber 110, or 112. Measurements 202 are detected from a radiation wavelength of interest for a particular gas. Upon determination, analyzer 210 may store concentration values 204 to memory (not shown), or optionally, report the concentration values 204 to a network. The control value may be a gain control value capable of indicating the amount of gain applied to each measurement 202 during each corresponding concentration value determination. The gain control value may be provided by calibrator 220 or located in memory accessible by analyzer 210.

Calibrator 220 automatically calibrates the analyzer 210 in response to initiation signal 302 from controller 300. In an embodiment, automatically calibrating the analyzer 210 comprises obtaining one or more concentration values 212 from the stream of concentration values 204 determined by analyzer 210, determining a calibration value 222 from the obtained concentration values 212, and providing the calibration value 222 to analyzer 210. Calibration value 222, optionally, is provided to a memory accessible by analyzer 210. In another embodiment, providing the calibration value 222 to analyzer 210 comprises replacing the control value with calibration value 222. Calibrator 220 optionally directs analyzer 210 to cease reporting concentration values 204 to the network in response to initiation signal 302. Upon completion of automatic calibration, calibrator 220 provides a status indicator 224 to controller 300.

Prior to determining the calibration value 222, calibrator 220 determines when a calibration gas equilibrates within sample chamber 110, 112. In one embodiment, the equilibrium is determined by allowing a predetermined amount of time to elapse using a timer. In another embodiment, calibrator 220 determines the equilibrium from a series of the obtained concentration values 212 using a comparator to determine when the successive concentration values are within some minimal difference or are no longer changing).

Controller 300 comprises an initiator 310 and an advisor 320, which may be incorporated within or located remotely to sensor 100. Although controller 300 and sensor electronics 200 are shown as separate entities, in some embodiments controller 300 may be integrated into sensor electronics 200. Initiator 310, when activated, is capable of initiating automatic calibration of sensor 100, preferably by providing an initiation signal 302 to calibrator 220. Initiator 310 can be a switch or button, activated manually or automatically, or an algorithm or interrupt executed by a dedicated processor or microcontroller.

Advisor 320 indicates that calibrator 220 has completed automatic calibration of sensor 100 in response to status indicator 224. In an embodiment, advisor 320 can be implemented as a three-state annunciator capable of indicating a "waiting for initiation" state when waiting for initiator 310 to be activated, a "currently calibrating" state after initiator 310 is activated and before receiving status indicator 224, and a "calibration complete" state upon reception of status indicator 224. As is well known in the art, there are many implementations of a three-state annunciator, including a multi-frequency sounder, a two-color LED, a one-color LED, multiple LEDs, a panel display, etc.

Controller 300, optionally, includes a restarter (not shown) capable of directing analyzer 210 to restart reporting concentration values 204 to the network. The restarter may be a switch or button, to be activated manually or automatically, or an automated algorithm or interrupt executed by a dedicated processor or microcontroller. Activation of the restarter, optionally, resets advisor 320 to the "waiting for initiation" state from the "calibration complete" state.

Figure 5:
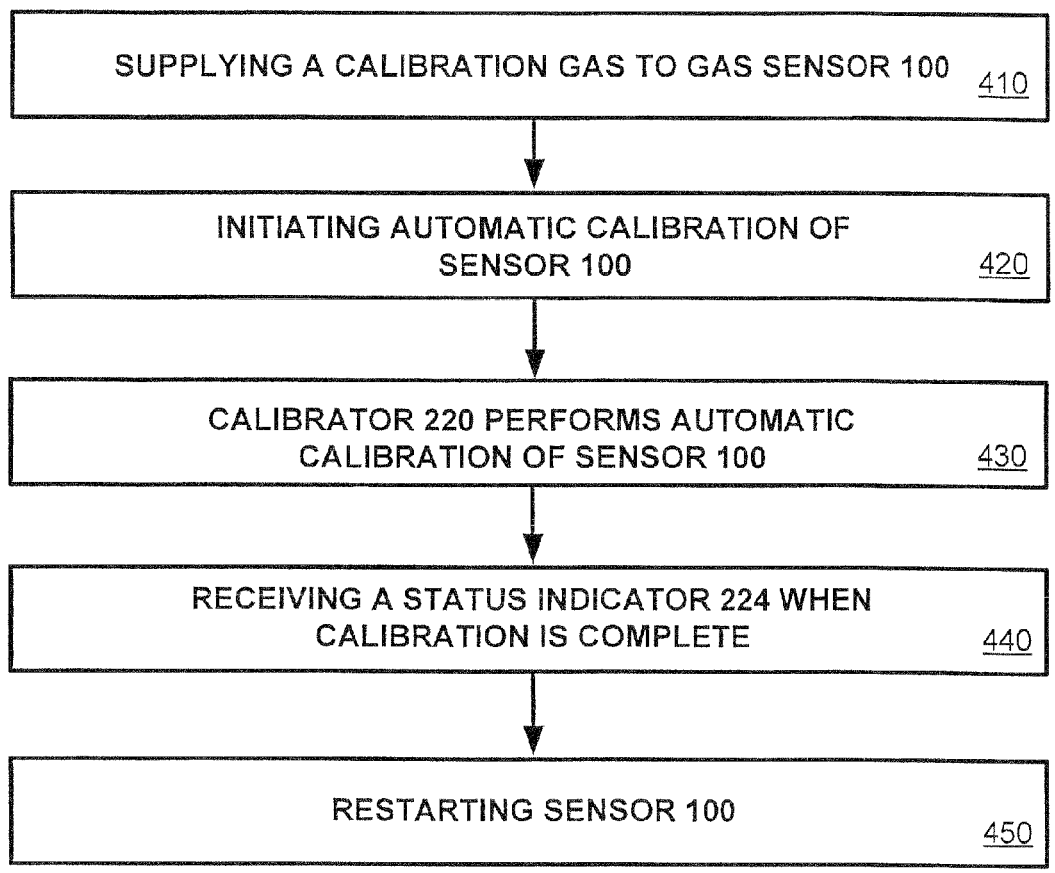
FIG. 5 contains a flow chart example for calibrating a sensor through sensor electronics and controller of FIG. 4.

FIG. 5 contains a flow chart 400 example for calibrating sensor 100 using the sensor electronics 200 and controller 300 of FIG. 3. The flow chart 400 is used for illustrating a method of the invention.

According to a block 410, a gas stimulus from a source (not shown) of a predetermined concentration is supplied to sensor 100 through gas port 150, or inlet tube 116. Although the gas stimulus can be supplied manually to sample chamber 110, the introduction of the gas stimulus can be controlled automatically tinder control of controller 300 or sensor electronics 200. Advisor 320 may display a "waiting for initiation" state during the performance of block 410.

According to a next block 420, automatic calibration of sensor 100 is initiated. In an embodiment, initiator 310, when activated, provides initiation signal 302 to calibrator 220, where initiation signal 302 is capable of initiating calibrator 220 to automatically calibrate sensor 100. Upon receipt of the initiation signal 302, calibrator 220 may direct analyzer 210 to cease reporting concentration values 204 to the network. Advisor 320 may display a "currently calibrating" state during the performance of block 420. Although block 420 is shown as being performed subsequent to block 410, their order of operation may be concurrent, overlapping, and in some instances reversed.

According to a next block 430, calibrator 220 performs automatic calibration of sensor 100. As will be discussed in further detail below with reference to FIG. 5, calibrator 220 may perform several steps in calibrating sensor 100, including obtaining one or more concentration values 204 determined by analyzer 210, determining when a gas stimulus reaches equilibrium within the sample chamber 110, determining a calibration value 222, and providing the calibration value 222 to analyzer 210.

According to a next block 440, upon completion of automatic calibration of sensor 100, controller 300 receives status indicator 224 capable of indicating that automatic calibration is complete. In an embodiment, advisor 320 receives status indicator 224 from calibrator 220, where advisor 320 displays a "calibration complete" state, or optionally, indicates to controller 300 that calibration is complete.

According to an optional block 450, analyzer 210 resumes the reporting of concentration values 204 to the network. Execution returns to block 410 where advisor 320 may display a "waiting for initiation" state. In an embodiment, block 450 is performed and execution returns to block 410 when the restarter within controller 300 is activated.

Figure 6:
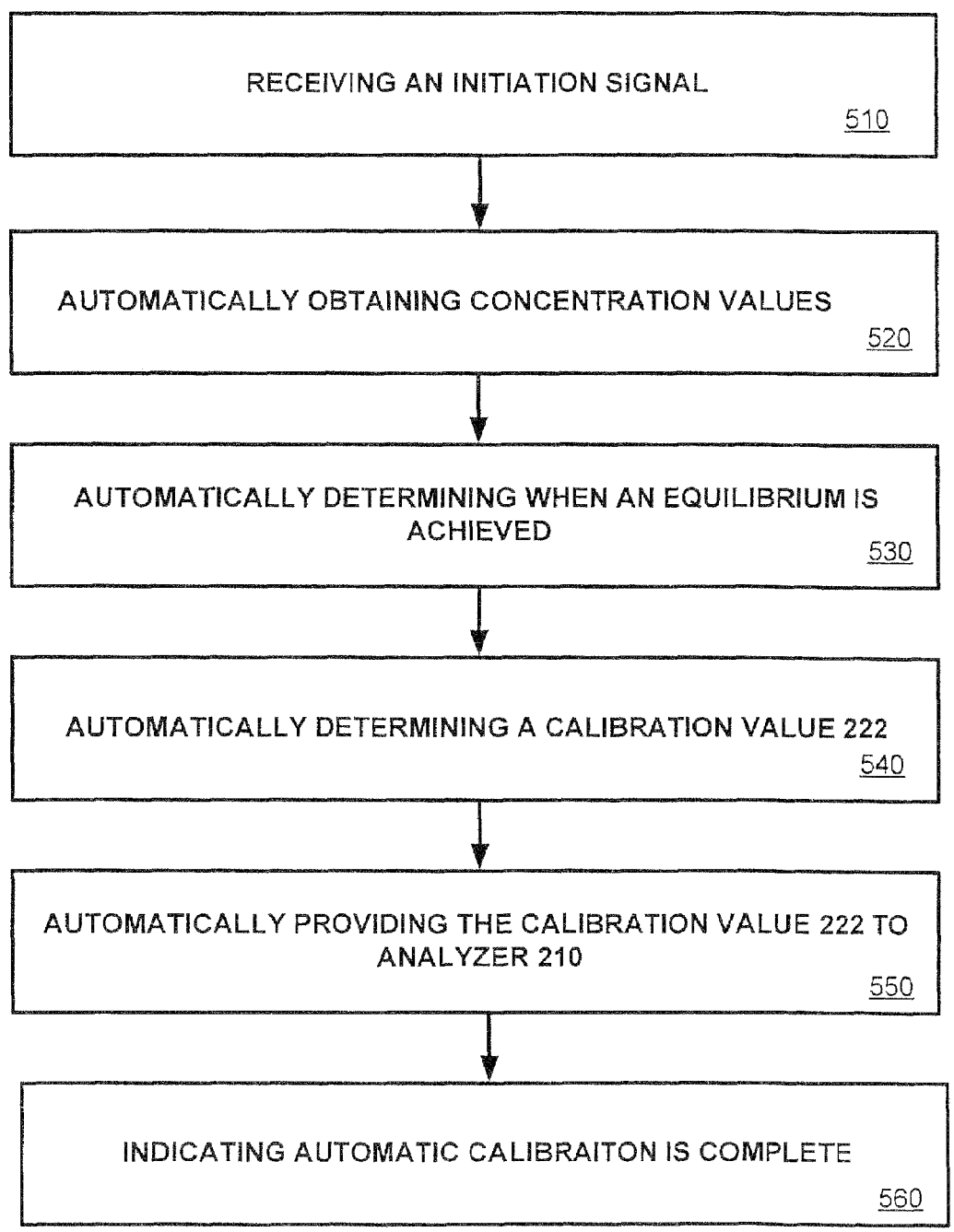
FIG. 6 contains a flow chart example for the operation of a calibrator of FIG. 4.

FIG. 6 contains a flow chart 500 example in more detail for the operation of calibrator 220 of block 430 of FIG. 4. The flow chart 500 is used for illustrating a method of the invention.

According to a block 510, calibrator 220 receives an initiation signal 302 from controller 300, where initiation signal 302 is capable of initiating calibrator 220 to automatically calibrate sensor 100. Initiator 310 within controller 300, preferably, provides the initiation signal 302 to calibrator 220. Upon receipt of the initiation signal 302, calibrator 220 may direct analyzer 210 to cease reporting concentration values 204 to the network.

According to a next block 520, calibrator 220 automatically obtains at least some of the concentration values 204 determined by analyzer 210. In an embodiment, calibrator 220 may obtain some of concentration values 204 through periodic sampling, with a preferred rate of one sample per second. Calibrator 220 may obtain concentration values 204 directly from analyzer 210, or from a memory capable of storing concentration values 204 from analyzer 210.

According to a next block 530, calibrator 220 automatically determines when a gas stimulus reaches equilibrium within the sample chamber 110 as determined either by a timer or by comparison of successive samples. In one embodiment, calibrator 220 determines equilibrium is achieved by allowing a predetermined amount of time to elapse. In another embodiment, calibrator 220 determines equilibrium is achieved from the obtained concentration values 212, preferably by computing the difference of each pair of contiguously obtained concentration values 212, maintaining a running average of the differences, and comparing the running average of the differences to a predetermined threshold. When the running average of the differences is less than the threshold, equilibrium is achieved. The predetermined threshold may be constant value stored in memory, or hard-wired within sensor electronic 200. Calibrator 220, optionally, resets the running average upon reception of initiation signal 302. Alternatively, successive values 212 can be subtracted or compared until the differences over selected time interval reach approximately zero, signifying equilibrium.

According to a next block 540, calibrator 220 automatically determines a calibration value 222. In an embodiment, calibrator 220 computes calibration value 222 with an iterative algorithm. The iterative algorithm may range from an elegant binary search used to minimize the computation time to a fixed interval search capable of minimizing the use of computational resources. In another embodiment, the calibration value 222 is within a predetermined error range of the known concentration of the calibration gas provided to sample chamber 110. The known concentration of the calibration gas may be stored in memory as a calibration gas concentration value. The predetermined error range may be constant value stored in memory, or hard-wired within sensor electronic 200.

According to a next block 550, calibrator 220 provides the calibration value 222 to analyzer 210. Calibration value 222 may be provided to a memory accessible by analyzer 210, where preferably the memory is non-volatile. In an embodiment, providing the calibration value 222 to analyzer 210 comprises replacing the control value with calibration value 222. According to a next block 560, calibrator 220 provides status indicator 224 to controller 300, where status indicator 224 is capable of indicating that automatic calibration is complete.

One of ordinary skill in the art will recognize that the concepts taught herein can be tailored to a particular application in many other advantageous ways. For instance, many equilibrium and calibration value 222 determinations may be implemented within sensor 100—it is acknowledged that, except where a specific determination is specified, the claims are intended to cover all such determinations. Radiation wavelengths "of interest" depend on the specific sensor application. Such minor modifications are encompassed within the invention, and are intended to fall within the scope of the claims.

The preceding embodiments are exemplary. Although the specification may refer to "an," "one," "another," or "some" embodiment(s) in several locations, this does not necessarily mean that each such reference is to the same embodiment(s), or that the feature only applies to a single embodiment.

Having described and illustrated the principles of the invention in various embodiments thereof, it should be apparent that the invention can be modified in arrangement and detail without departing from such principles. I claim all modifications and variations coming within the spirit and scope of the following claims.

The invention claimed is:

1. A method of operating a calibrator, the method comprising:
   receiving an initiation signal capable of initiating the calibrator;
   automatically obtaining concentration values in response to the initiation signal;
   automatically determining when a calibration gas equilibrates within a sample chamber; and automatically determining a calibration value from the obtained concentration values.

2. The method of claim 1, where determining when the calibration gas equilibrates within the sample chamber comprises:
- determining a difference value for each pair of contiguously obtained concentration values;
- averaging the difference values; and
- comparing the average of the difference values to a predetermined threshold.

3. The method of claim 1, where determining when the calibration gas equilibrates within the sample chamber comprises allowing a predetermined amount of time to elapse.

4. The method of claim 1, where the calibration value is determined using an iterative algorithm.

5. The method of claim 4, where the calibration value is within a predetermined error range corresponding to a calibration gas concentration.

6. The method of claim 1, further comprising automatically indicating the calibrator has determined the calibration value.

7. A computer-readable medium containing computer instructions that, when executed, cause a processor or multiple communicating processors to perform a method for calibrating a sensor, the method comprising:
- receiving an initiation signal capable of initiating the calibrator;
- obtaining concentration values in response to the initiation signal;
- determining when a calibration gas equilibrates within a sample chamber; and
- determining a calibration value from the obtained concentration values.

8. The method of claim 7, further comprising:
- receiving measurements of detected radiation at least at a radiation wavelength of interest; and
- determining the concentration values in response to the measurements.

9. The method of claim 7, further comprising generating the initiation signal.

* * * * *